United States Patent [19]

Katsuhiko et al.

[11] Patent Number: 4,804,262
[45] Date of Patent: Feb. 14, 1989

[54] AUTOMATIC PERIMETER

[75] Inventors: Kobayashi Katsuhiko, Itabashi; Shioiri Takashi, Wako; Tago Hideo, Matsudo, all of Japan

[73] Assignee: Tokyo Kogaku Kikai Kabushiki Kaisha, Tokyo, Japan

[21] Appl. No.: 718,896

[22] Filed: Apr. 2, 1985

[30] Foreign Application Priority Data

Apr. 3, 1984 [JP] Japan .................................. 59-66034
May 15, 1984 [JP] Japan .................................. 59-96988

[51] Int. Cl.$^4$ .............................................. A61B 3/02
[52] U.S. Cl. .................................................. 351/226
[58] Field of Search ........................ 351/224, 225, 226

[56] References Cited

U.S. PATENT DOCUMENTS

| 3,883,234 | 5/1975 | Lynn et al. | 351/224 |
| 4,255,022 | 3/1981 | Kuether et al. | |
| 4,346,968 | 8/1982 | Melin et al. | 351/224 |
| 4,429,961 | 2/1984 | Sheingorn | 351/224 X |

OTHER PUBLICATIONS

"Automatic Perimetry in Glaucoma Visual Screening", pp. 21-37, Albrecht von Graefe's Archive for Clinical and Experimental Ophthalmology, 1.IV., 1976 (Springer Verlag, New York).
Acta Ophthalmologica, vol. 53,-1975, pp. 293-310, "An Automatic Static Perimeter, Design and Pilot Study", by A. Heiji & C. E. T. Krakau.

*Primary Examiner*—Rodney B. Bovernick
*Attorney, Agent, or Firm*—Brumbaugh, Graves, Donohue & Raymond

[57] ABSTRACT

An automatic perimeter comprising stimulus presentation unit for presenting stimuli to examine a patient's eyesight, an examination program memory for memorizing a plurality of examination programs which present stimuli under different presentation conditions, a selector for selecting a first examination program for the first examination, and a presentation controller for controlling said stimulus presentation unit so that stimulus presentation for said first examination is carried out under a presentation program selected by a selecting command if the selecting command is applied to the selector and carried out under a predetermined presentation program if the selecting command is not applied to the selector.

6 Claims, 5 Drawing Sheets

AUTOMATIC PERIMETER

BACKGROUND OF THE INVENTION

1. Field of the Invention

The present invention relates to an automatic perimeter for automatically examining the field of vision of a patient's eye. More specifically, the present invention pertains to an automatic perimeter which is designed to automatically present marks or stimuli in accordance with various conditions including brightness, positions, presentation time and presentation intervals of the stimuli.

2. Description of the Prior Art

In general, a perimeter has a hemispherical concave screen on which stimuli are presented. In such perimeter, a patient's eye to be examined is located at the center of the sphere of the screen and the sight axis of the eye is fixed at the center of the screen by having the eye focus on a fixed viewing target on the screen. Then, the stimuli are presented in accordance with various conditions in sequence at various positions on the screen with different sizes and different brightness so as to distinguish visible zones from invisible zones.

Meanwhile, conventional automatic perimeters have a plurality of examination programs for stimulus presentation, for example, a screening examination program, a meridional examination program for longitudinal examination, and a glaucoma examination program. The perimeter is designed so that it reads a specific program or a first stimulus presentation program at the beginning of each examination. It has been common to have the program preliminarily determined by a manufacturer in view of the fact that it is frequently used as a first examination and the burden imposed on the operator can be decreased by preliminarily determining the program.

It should, however, be noted that problems have been encountered in that the first stimulus presentation program cannot be exchanged although there may be differences in the most frequently used programs for the first examinations among different treatments and examinations, such as the screening examination programs for group examinations, the meridional examination programs for generally ophthalmic examinations, or the glaucoma examination programs for adult disease examinations. In other words, the perimeter is designed so as to read the predetermined program is not at the beginning of examination, but the program is not at all used, so that the automatic perimeter mentioned above is inconvenient compared with the manual perimeter.

Other conventional automatic perimeters are designed so that a stimulus presentation program is adapted to present 50 through 200 stimuli and the presentation is carried out at random in accordance with the output of a random number generator in order to eliminate measuring errors resulting from the patient being able to predict the presentations of the stimuli. However, such a perimeter is disadvantageous in that the presentation cannot be suspended once it is started.

Conventionally, there has been proposed an automatic perimeter in which presentations of the stimuli can be suspended. In such a perimeter, the examination data obtained before the interruption of presentation of the stimuli are not presented at the output once the presentations of the stimuli are suspended, from the viewpoint that the stimuli are presented over the whole sphere of the screen in accordance with random numbers so that these data are considered not to be enough to obtain an accurate result of examination.

In general, patients suffer fatigue from these types of examinations and, therefore, it is preferable to have the examinations completed as quickly as possible. However, with the aforementioned types of conventional perimeters, it is impossible to have the examination terminated even when a malady of the patient's eye has been detected and further examination has become no longer necessary.

Further, there is known an automatic perimeter having a supplemental lens which is adapted to be inserted in front of the patient's eye. This type of perimeter is designed for examinations of eyes having extreme anomalies of refraction, for example, hyperopia and myopia. In this type of perimeter, inconveniences have been encountered in that the sphere in which the stimuli are presented has an angular extension which is so large that the patient cannot watch the stimuli presented on peripheral areas of the sphere through the supplemental lens. If the examination is carried out throughout the angular extension of the sphere through the supplemental lens, no examination data can be obtained in the peripheral areas since the field of vision is limited by the lens frame. In order to eliminate the problem, these types of perimeters have two stimulus presentation programs, one being a central zone program which covers the central area of the sphere where the patient can watch the stimuli through the supplemental lens, and a peripheral zone program where the stimuli are to be watched without the supplemental lens. It should however be noted that perimeter is inconvenient to use because the operator must move the supplemental lens into and out of the patient's sight axis manually, incurring a risk that the operator may even fail sometimes to operate the supplemental lens, and the operator must combine the data obtained through the two programs to make the judgment.

OBJECT OF THE INVENTION

It is therefore an object of the present invention to provide an automatic perimeter in which stimulus presentation program used for the first examination can be selected by the operator, and a predetermined program is read out as the first examination unless the operator does not select another program.

Another object of the present invention is to provide as automatic perimeter in which stimulus presentation can be suspended, and at the same time, the operator can obtain the result of examination through data obtained before suspending the presentation and which can also eliminate errors resulting from the patient's prediction of presentations of the stimuli.

A further object of the present invention is to provide an automatic perimeter in which the operator can move without fail a supplemental lens into and out of the patient's sight whenever necessary.

SUMMARY OF THE INVENTION

According to present invention, the above and other objects can be accomplished by an automatic perimeter comprising stimulus presentation means for presenting stimuli to examine a patient's eyesight, examination program memory means for memorizing a plurality of examination programs which present stimuli under different presentation conditions, selecting means for selecting a first examination program for the first examination, and presentation means. The presentation control means controls said stimulus presentation means so that stimulus presentation for said first examination is carried out under a presentation program selected by a selecting command when said selecting command is applied to said selecting means, and under a predetermined presentation program when said selecting command is not applied to said selecting means.

In a preferable aspect of the present invention, said predetermined presentation program is a glaucoma examination program.

According to a specific aspect of the present invention, there is provided an automatic perimeter comprising stimulus presentation means having a plurality of stimuli, presentation condition memory means for memorizing at least one specific presentation program in which stimuli are presented on a specific area in a higher density than on other areas, stimulus presentation control means for controlling said stimulus presentation means so that said specific program is read at first, then outer presentation programs are read, and stimulus presentation is interrupted. The invention further includes a response means for inputting perception signals in response to said stimuli, response memory means for memorizing said perception signals together with their presentation condition, and output means for producing an output based on the data memorized in said response memory means.

In a preferable aspect of the present invention, said specific area comprises an area between circles of sighting angles 10° and 20° and an area stretching outwardly from a point corresponding to a blind spot.

In another aspect of the present invention, said stimulus presentation control means has a random number generator so that stimulus presentation in each presentation program is carried out at random in accordance with the output of said generator.

According to another aspect of the present invention, there is provided an automatic perimeter comprising stimulus presentation means for presenting stimuli, supplemental lens means inserted into and removed from an axis of an eye to be examined so that anomalies of refraction of said eye are compensated for, stimulus presentation condition memory means for memorizing stimulus presentation routines for a center area and a peripheral area of stimulus presentation field. The perimeter further includes routine progress means for controlling the progress of said routines, and control means for producing presentation control signals in accordance with said stimulus presentation routines, said routine progress means including means to stop said routine when said routine is completed.

In a further preferable aspect of the present invention, said means to stop said routine includes means to proceed to a next routine when said routine is completed and said supplemental lens means is removed from said axis.

The above and other objects and features of the present invention will become apparent from the following description of a preferred embodiment with reference to the accompanying drawings.

DESCRIPTION OF THE PREFERRED EMBODIMENT

Figure 1:
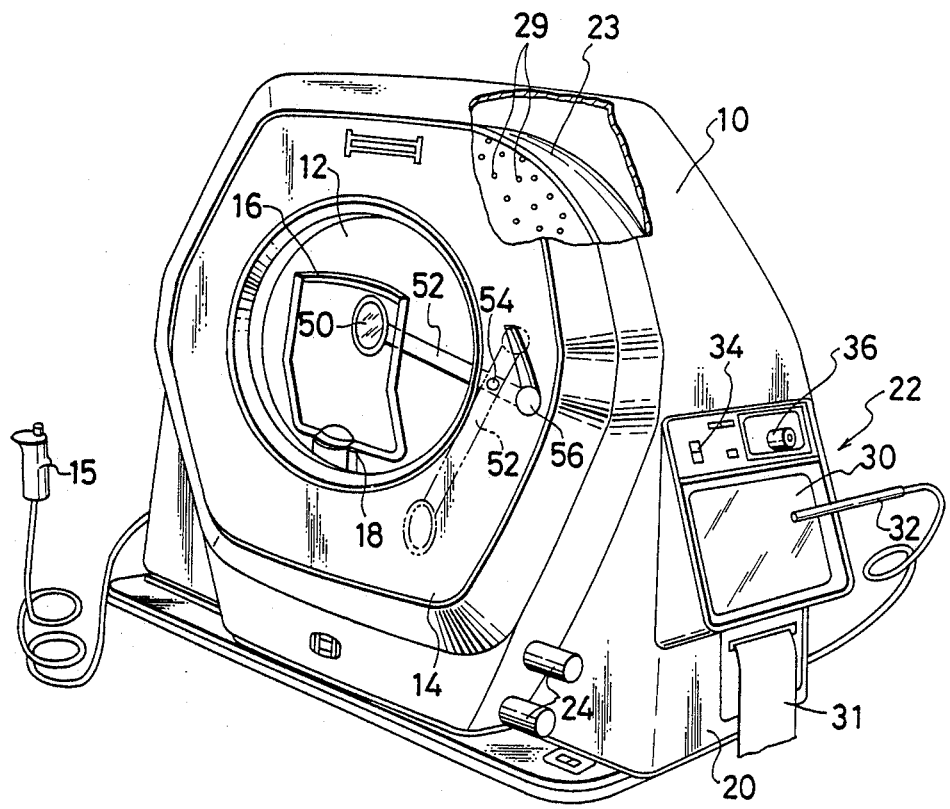
FIG. 1 is a prespective view showing the automatic perimeter in accordance with one embodiment of the present invention.

Referring now to the drawings, there is shown an automatic hemispherical perimeter in which the present invention is embodied. The automatic perimeter shown in FIG. 1 includes a housing 10, a panel 14 mounted on the housing 10 at its front side and having an opening 12 through which a patient's head goes in, a perception switch 15 operated by the patient, a front support 16 and a chin-rest 18 adjustably mounted in the housing 10 for locating the patient's face, and a control and display apparatus 22 as mentioned hereafter. There are provided hand grips 24 for horizontally and vertically adjusting the front support 16 and the chin-rest 18 on the housing 10 at its lower side. There is also provided a hemispherical screen 23 in the housing 10 directed against the opening 12.

The screen 23 has a plurality of light-emitting diodes LED 29 which are arranged on its whole inner surface in such a manner that they form a matrix to generate a plurality of stimuli and a fixation electroluminescence diode provided at a center of its inner surface for fixing the sight axis of the patient.

The control and display apparatus 22 includes a TV monitor 30, a light pen 32, a printer 31 located under the monitor 30, a control switch 34 located over the monitor 30, and a telescope 36 positioned over the monitor 30 for watching the fixation of the patient's sight axis. The monitor 30 displays the kind, size, brightness and distribution of stimuli, and different control commands as mentioned hereafter.

The printer 31 prints the result of the eyesight examination. The telescope 36 is constituted so as to permit the front portion of the patient's eyes to be watched through an orifice provided at a position substantially the same as that of the fixation diode, so the operator can observe through the telescope 36 whether or not the sight axis is fixed at the fixation diode.

There is further provided a supplemental lens 50 supported by a swing arm 52 in the housing 10 so that the patient suffering from anomalies of refraction can perceive the stimuli presented on the screen 23 in its center area through the supplemental lens 50. Of course, since different people have different eyesight or optical problems, the supplemental lens 50 is a lens selected from various lenses, according to a patient's needs, and removably inserted on the arm 52 in the conventional manner. The swing arm 52 is swingingly supported on the housing 10 by a pin 54, whereby the supplemental lens 50 is located either at an inserted position (shown by a solid line in FIG. 1) where it is positioned on the patient's sight axis, or at a removed position (shown by a broken line in FIG. 1) where it is positioned off the patient's sight axis. The swing arm 52 is held by holding means (not shown in Figures) at both positions where the lens 50 is adapted to be located at the inserted position and the removed position. There is provided a knob 56 projecting from the end of the swing arm 52 through the panel 14 to swing the swing arm 52, and a supplemental lens detector (not shown in the Figures) mounted near the arm 52 is positioned at the inserted position to detect whether or not the lens 50 is inserted into the patient's sight axis.

In the aforementioned perimeter, the patient's head is rested on the front support 16 and the chin-rest 18 which are adjusted by the hand grips 24 to position the patient's eye at the center of the hemisphere of the screen 23.

The fixation diode is then lit to fix the patient's sight axis at the fixation diode, and the stimuli are successively presented on the screen 23 to examine the patient's eyesight while the fixation of the sight axis is checked through the telescope 36. If the patient has the anomalies of refraction, he watches the stimuli presented in the center are of the screen 23 through the lens 50 and the stimuli presented in the peripheral area of the screen without the lens 50.

The patient depresses a button of the perception switch 15 when he perceives the stimulus, and a response memory means as mentioned hereafter memorizes the perception in relation to the condition in which the perceived stimulus was presented. The patient's eyesight is determined by collating the data of the perceptions and the stimulus presentation conditions memorized as above.

The control commands adopted in the perimeter are as follows:

(1) Selection of examination program, such as a screening program to examine the whole of the sight field by using screened stimuli, or a meridional program to examine meridional directions. Selection is done by the light pen 32 before the presentation.

(2) Determination of main characteristics of the stimuli such as luminance, presentation time, and interval of presentation. These are given by the light pen 32 before the presentation.

(3) Execution of the examination program as selected. This is done using the light pen 32 or the control switch 34.

(4) Stopping the examination program. This is done by the control switch 34 or the light pen 32 during the stimulus presentation.

(5) Recommencement of the examination program from its stopped presentation step following the interruption. This is always done using the light pen 32 or the control switch 34 during interruption of the stimulus presentation.

(6) Printing a result of the examination. This is done using the light pen 32 or the control switch 15 after the examination is completed.

Figure 2:
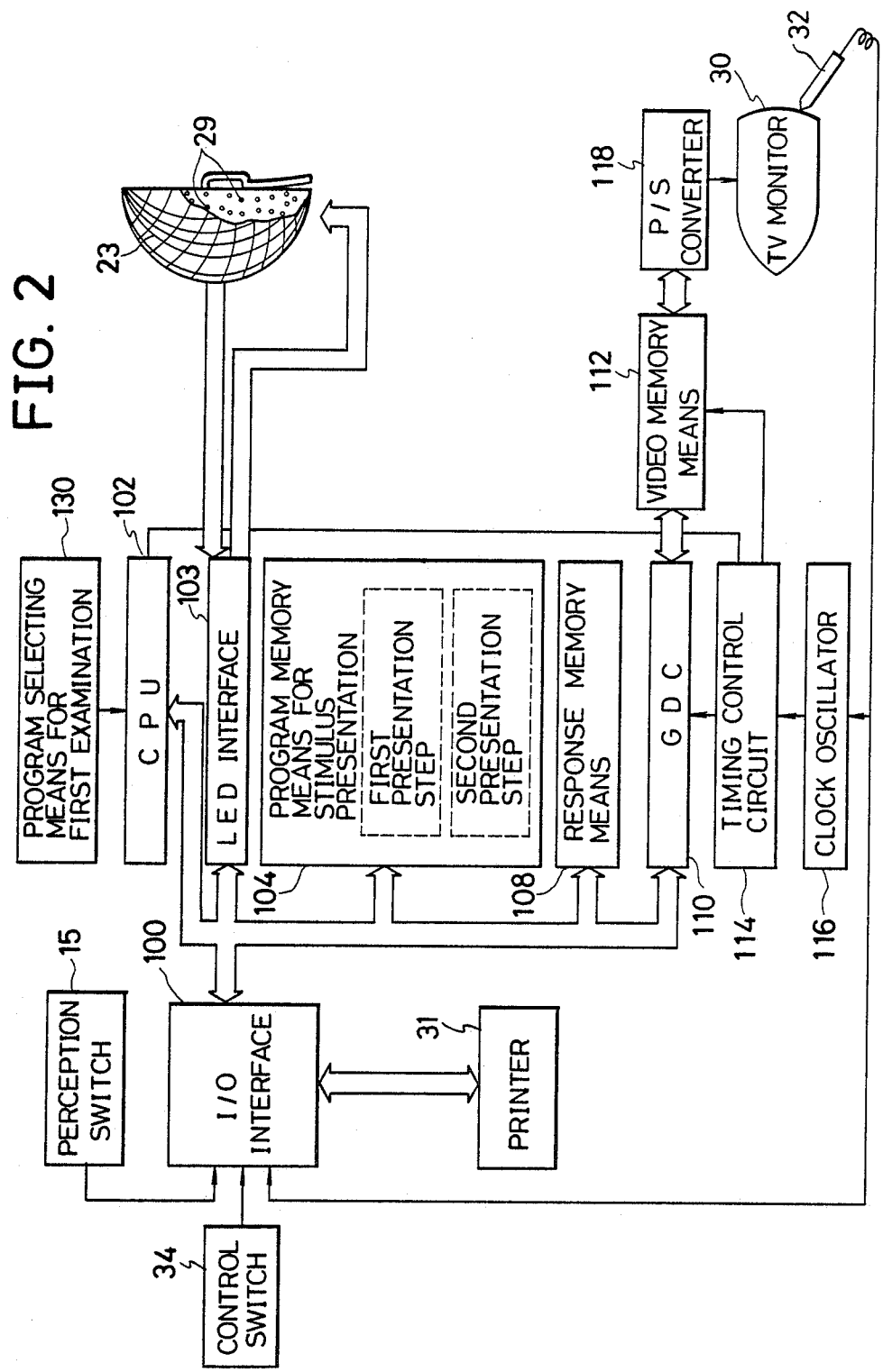
FIG. 2 is a block diagram of the control system adopted in the embodiment show in FIG. 1.

A control system of the perimeter, as shown in FIG. 2, includes an input/output interface (called an "I/O interface" hereinafter) 100 having an input connected with the perception switch 15, the control watch 34 and the light pen 32. The I/O interface 100 also has a terminal connected with a central processing unit (CPU) 102, a LED matrix interface (called a "LED interface" hereinafter) 103, program memory means for stimulus presentation 104, response memory means 108, a graphic display controller (GDC) 110 and a printer 31. The I/O interface 100 functions to convert signals received through the input into signals appropriate for the functions of the aforementioned internal elements and printing is carried out by the printer 31. GDC 110 may be NEC Co. Model $\mu$ PD 7220.

The CPU 102 has an input connected with the LED interface 103, the program memory means 104, the response memory means 108, the GDC 110 and program selecting means for first examination 130, and functions to perform main control of the perimeter as mentioned hereafter.

The LED interface 103 has a matrix composed of at least two transistor arrays to light the LED under a predetermined stimulus presentation condition taken from the CPU 102. The program memory means 104 memorizes a plurality of examination programs, for example, a screening examination program, a meridional examination program, and a glaucoma examination program. Each program is formed to combine the stimulus presentation conditions such as lighting time, and lighting interval, with the characteristics of the stimuli such as brightness.

Figure 3:
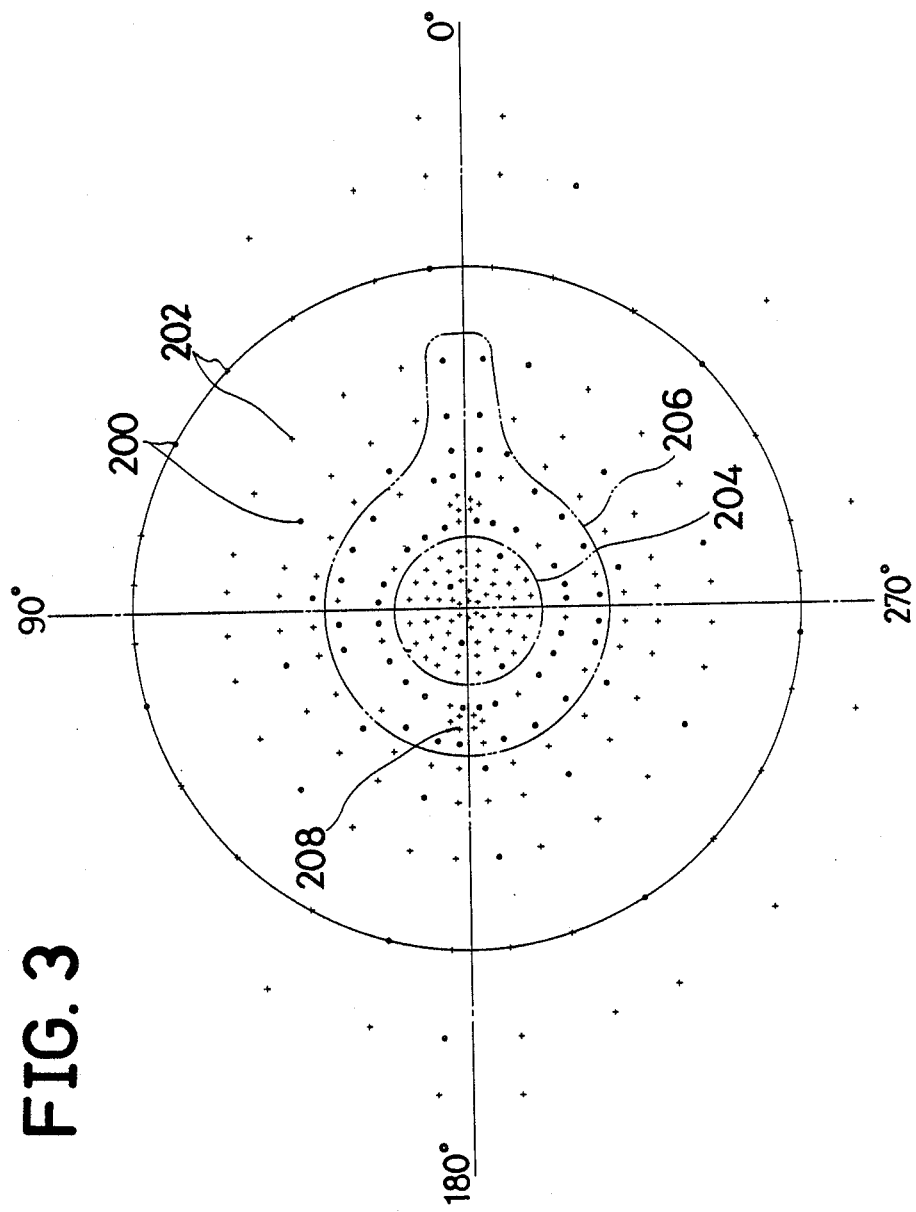
FIG. 3 is a schematic distribution chart of stimuli.

In the glaucoma examination program, the stimuli for the patient's left eye to be examined, as shown in FIG. 3, are divided into stimuli 200 indicated by dots and stimuli 202 indicated by crosses. The density of the stimuli 200 is higher in an area between a circle 204 of sighting angle 10° and a circle 206 of sighting angle 20° (Bjerrum area) and an area stretching outwardly from a point 208 corresponding to a blind spot (Nasalstep area) than in other areas, because a sight defect caused by glaucoma tends to mainly appear in these areas so that the glaucoma is generally detected and examined by an eyesight examination of these areas.

The stimuli 202 consist of all stimuli used for conventional eyesight examination other the stimuli 200.

When the patient has the anomalies of refraction, the stimuli 200 are watched by the patient through the lens 50 and the stimuli 202 are watched by the patient without the lens 50. In other examination programs, the stimuli are also divided into those presented in the first presentation condition to be watched through the lens 50 and those presented in the second presentation condition to be watched without the lens 50.

The order of presentation of the stimuli is controlled by a random number generator (not shown in the Figures) so that the patient cannot predict the stimuli which will be presented therefore giving a precise eyesight examination.

FIG. 3, as mentioned above, shows the stimulus position for the left eye, and the stimulus distribution for the right eye is obtained by reversing the distribution shown in FIG. 3 so that the Nasalstep area is at the left.

The response memory means 108 memorizes the presentation conditions of the presented stimuli when the patient depresses the button of the perception switch 15 in accordance with his perception of the stimulus. The GDC 110 receives a stimulus presentation signal, a selected examination program signal, a position signal of the lit stimulus and the response signal from the I/O interface 100, and functions to produce image signals which display information of said signals on the monitor 30. The GDC 110 has an output connected with a video memory means 112 and applies the image signals to the video memory 112.

A timing control circuit 114 has an input connected with a clock oscillator 116 and an output connected with the CPU 102, the GDC 110 and the video memory 112, and functions to produce predetermined timing signals in accordance with clock signals take from the clock oscillator 116. The timing signals are applied to the CPU 102, the GDC 110 and the video memory 112.

A parallel-serial converter (called "P/S converter" hereinafter) 118 has an input connected with the video memory 112 and an output connected with the monitor 30, and carries out parallel-serial conversion to convert parallel digital signals taken from the video memory 112 into serial video signals applied to the monitor 30. The program selecting means for first examination 130 is actuated by the operator to select the stimulus presentation program for the first examination.

Figures 4, 4A:
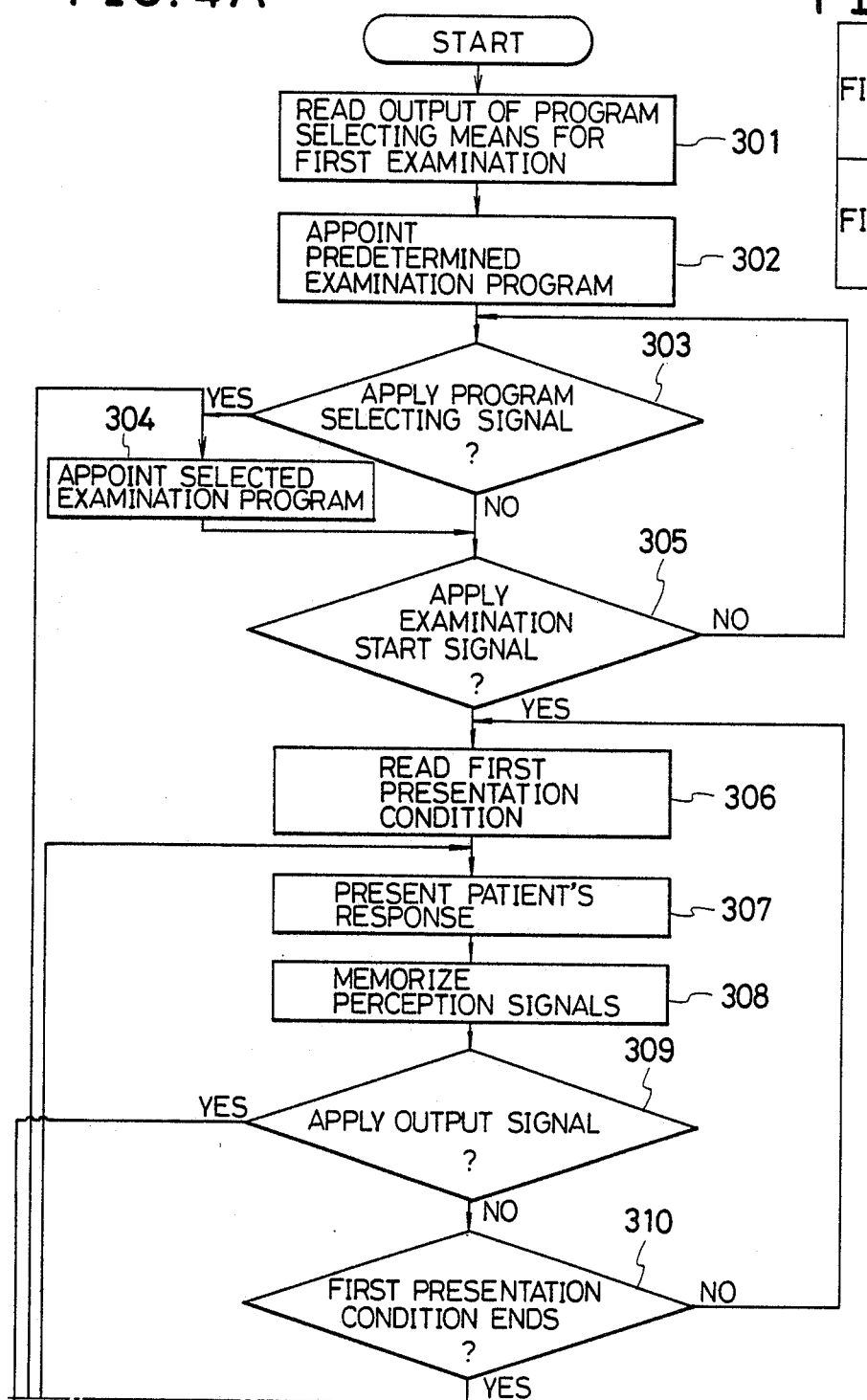
FIG. 4 is a flow chart showing overall operation of the aforementioned embodiment.
Figure 4B:
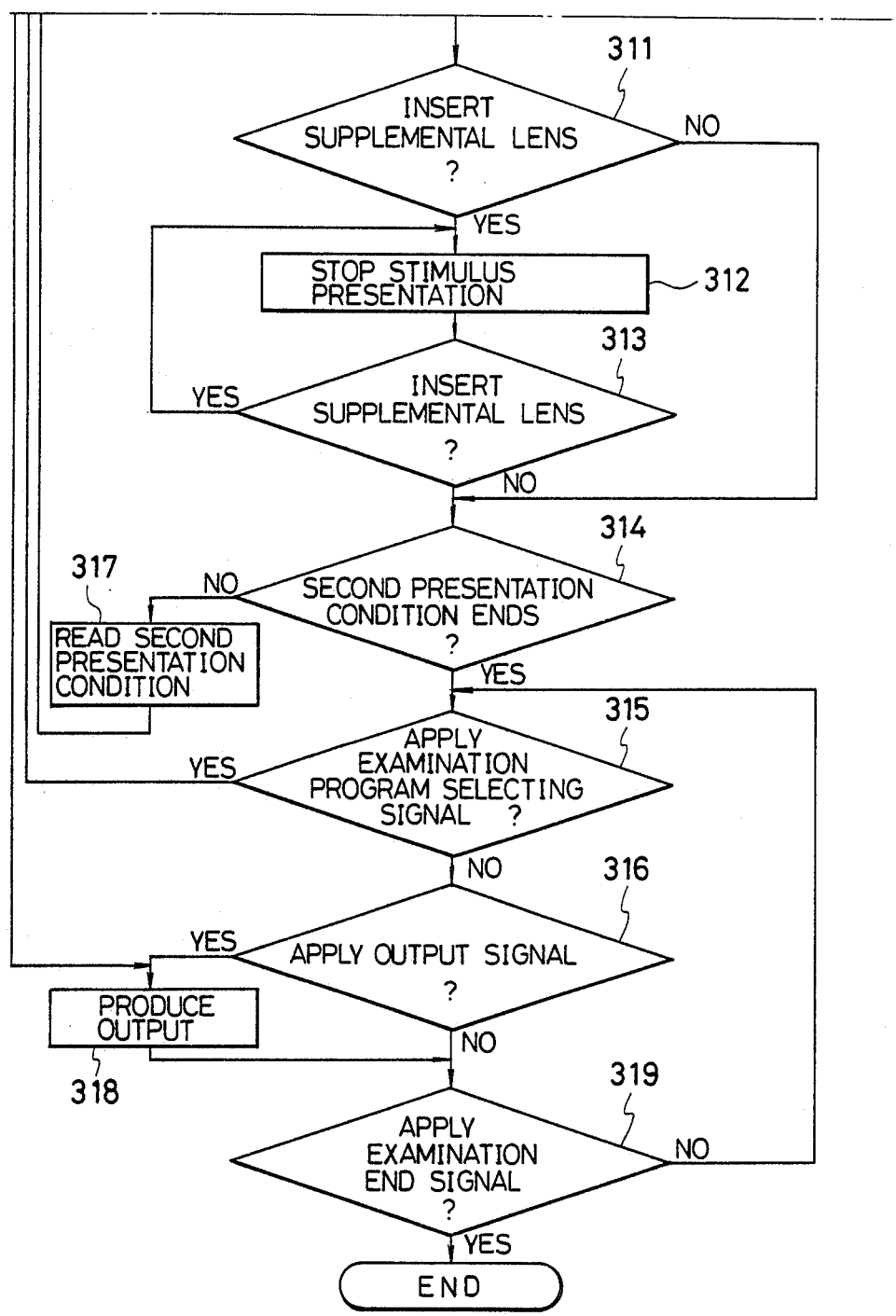

Referring now to FIG. 4, there is shown the function of the perimeter mentioned above. After a source switch is turned on, the operator actuates the program selecting means for first examination 130 to select a examination program before beginning the examination when he wants to first examine the patient's eyesight by an examination program other than the examination predetermined by the CPU 102 for the first examination.

In a step 301, the CPU 102 reads an output of the program selecting means 130. In a step 302, the examination program predetermined for the first step is designated in the program memory means 104 for the first examination. In a step 303, the CPU 102 judges whether or not a program selecting signal is applied to the program selecting means 130. If the program selecting signal is not applied thereto, the judgement on whether or not an examinaton start signal is input through the light pen 34 or the control switch 38 is made in a step 305. If the program selecting signal is applied thereto, the selected examination program is appointed in the program memory means 104 for the first examination in place of the predetermined program in a step 304 and after that the step 305 is carried out.

When the examination start signal is applied thereto, there takes place step 306 where the first presentation condition of either the predetermined examination program or the selected examination is read, and in a step 307 the stimuli are presented to the patient in accordance with the first presentation condition in such a manner that the LEDs 29 are successively lit. In a step 308 the patient's responses to the stimulus presentation are applied to the response memory means 108 through the perception switch 15 to memorize the response together with the stimulus presentation condition.

On the other hand, while observing the stimulus presentation and the patient's response, the operator is always able to apply an output signal through the light pen 34 or the control switch 38 to the CPU 102 during the stimulus presentation in order to stop the examination. In a step 309 judgement is made on whether or not the CPU 102 receives the output signal. If the CPU 102 does not receive the output signal, the function is advanced to a step 310 where the judgement is made on whether or not the presentation under the first presentation condition is completed. If the CPU 102 receives the output signal, the function is advanced to a step 318 mentioned hereafter.

When the CPU 102 judges that the presentation under the first presentation condition is completed, the judgement is made on whether or not the supplemental lens 50 is located at the inserted position in a step 311. If the presentation under the first presentation condition is not completed, the function is returned to the step 306.

If the lens 50 is located at the inserted position in the step 311, the first presentation is stopped on the step 312 and the judgement is made as to whether or not the lens 50 is located at the inserted position in step 313 again. When the lens 50 is located at the inserted position in the step 313, the function is returned to the step 312 so that the stimulus presentation is stopped until the lens 50 is located at the removed position. When the CPU 102 judges that the lens is not located at the inserted position in either step 311 or 313, the function is advanced to a step 314 where the judgement on whether or not the second presentation condition is completed.

When the presentation under the second presentation condition is not completed, the function is returned to the step 307 through the step 317 where the second presentation condition is read out from the program memory means 104. If the presentation under the second presentation condition is completed, a step 315 judging whether or not the program selecting signal applied to the CPU 102 is carried out. If the CPU 102 in the step 315 judges that the program selecting signal is applied thereto, the function is returned to the step 304. Meanwhile, if the CPU 102 judges that the program selecting signal is not applied thereto, the function is advanced to a step 316, making the judgement whether or not the output signal is applied to the CPU 102.

The function is advanced to a step 319 through a step 318 producing output when the judgement in the step 316 is YES, and the function is directly advanced to the step 319 when the judgement in the step 316 is NO. In the step 319, the judgement on whether or not an examination end signal is inputted to the CPU 102 is made. The function is returned to the step 315 when the judgement in the step 319 is NO, and the function is finished when the judgement in the step 319 is YES.

It should be understood that while the invention has been described with respect to the preferred embodiment, variations may be perceived by those skilled in the art while nevertheless not departing from the scope of the present invention as described by the claims appended hereto.

We claim:

1. An automatic perimeter for examining a patient's eyes, comprising:
   stimulus presentation means for presentation of first and second groups of different stimuli onto a stimulus presentation field, the stimuli of the first group contributing more to the examination of vision field than the stimuli of the second group;
   presentation condition memory means for memorizing a presentation program for presenting on said field during a first examination period more stimuli of the first group than of the second group and for presenting on said field during a second examination period more stimuli of the second group than of the first group;
   stimulus presentation control means for controlling said stimulus presentation means under said presentation program;
   response means for inputting perception signals initiated by a patient in response to said stimuli;
   response memory means for memorizing said perception signals together with their presentation condition; and
   output means for producing an output based on the data memorized in said response memory means during and after execution of said program,
   said stimulus presentation control means being responsive to memorizations by said response memory means of sufficient data for examination of the field of vision of the patient's eye to interrupt the stimulus presentation program before it is completed.

2. An automatic perimeter in accordance with claim 1 in which said presentation memory means contains a stimuli presentation program for presenting stimuli on a specific area of said field in a higher density than on other areas, said specific area comprising an area between circles of sighting angles of 10° and 20° and an area stretching outwardly from a point corresponding to a blind spot.

3. An automatic perimeter in accordance with claim 1 in which said stimulus presentation control means has a random number generator so that stimulus presentation is each presentation program is carried out at random in accordance with output of said generator.

4. An automatic perimeter for examining a patient's eyes, comprising:
   stimulus presentation means for presenting stimuli onto a stimulus presentation field;
   supplemental lens means mounted for movement into or away from the patient's sight axis to a reference location on said field to compensate for anomalies of refraction of the patient's eye;
   stimulus presentation condition memory means for memorizing stimulus presentation routines for a center area and a peripheral area of said stimulus presentation field;
   routine progress means for controlling the progress of said routines, said routine progress means including means to suspend said routine when said routine is completed; and
   control means for producing presentation control signals in accordance with said stimulus presentation routines for suspending stimulus presentation between the stimulus presentation for a center area and the stimulus presentation for a peripheral area of said stimulus presentation field during which time said supplemental lens means is moved into or away from the patient's sight axis.

5. An automatic perimeter in accordance with claim 4 in which said means to suspend said routine includes means for proceeding to a next routine when said routine is completed and said supplemental lens means is removed from the patient's sight axis.

6. An automatic perimeter for examining a patient's eyes, comprising:
   stimulus presentation means for presenting stimuli onto a stimulus presentation field;
   supplemental lens means, mounted for movement into or away from the patient's sight axis to a reference location at said field, to compensate for eye defects in a patient being examined;
   stimulus presentation condition memory means for memorizing stimulus presentation routines for a center area and a peripheral area of said stimulus presentation field;
   routine progress means for controlling the progress of said routines, said routine progress means being arranged to suspend production of presentation control signals after changing said areas of stimulation presentation field, upon movement of said supplemental lens into the patient's sight axis, and to resume progress of said routines upon movement of said supplemental lens out of the patient's sight axis; and
   control means for producing presentation control signals in accordance with said stimulus presentation routines.

* * * * *